United States Patent [19]
Korth

[11] Patent Number: 5,895,785
[45] Date of Patent: Apr. 20, 1999

[54] TREATMENT AND PREVENTION OF DISORDERS MEDIATED BY LA-PAF OR ENDOTHELIAL CELLS

[75] Inventor: Ruth Korth, Palestrinastr. 7A, D-80639 München, Germany

[73] Assignee: Ruth Korth, Munich, Germany

[21] Appl. No.: 08/938,357

[22] Filed: Sep. 29, 1997

Related U.S. Application Data

[63] Continuation of application No. 08/444,103, May 18, 1995, abandoned, and a continuation-in-part of application No. 08/104,599, Aug. 11, 1993, Pat. No. 5,480,881, application No. 08/261,765, Jun. 17, 1994, Pat. No. 5,605,927, and application No. 08/246,476, May 19, 1994, Pat. No. 5,696,114, said application No. 08/444,103, is a continuation-in-part of application No. 08/172,234, Dec. 23, 1993, Pat. No. 5,530,023, which is a continuation-in-part of application No. 07/994,752, Dec. 22, 1992, abandoned, and application No. 07/845,088, Mar. 3, 1992, Pat. No. 5,356,791, which is a division of application No. 07/704,554, May 23, 1991, abandoned, said application No. 08/104,599, is a continuation of application No. 07/844,882, Mar. 3, 1992, abandoned, said application No. 08/261,765, is a continuation-in-part of application No. 07/969,674, Oct. 28, 1992, Pat. No. 5,346,894, and application No. 07/968,878, Oct. 30, 1992, abandoned, said application No. 08/246,476, is a continuation of application No. 07/968,878.

[30] Foreign Application Priority Data

| Oct. 20, 1987 | [DE] | Germany | 37 35 525 |
| Jun. 1, 1990 | [DE] | Germany | 40 17 818 |
| Oct. 26, 1990 | [DE] | Germany | 40 34 090 |
| Nov. 4, 1991 | [EP] | European Pat. Off. | 91118744 |
| Nov. 4, 1991 | [EP] | European Pat. Off. | 91118745 |
| Dec. 28, 1992 | [DE] | Germany | 42 44 265 |

[51] Int. Cl.$^6$ .................... A61K 31/55; A61K 31/34; A61K 31/225

[52] U.S. Cl. .................... 514/219; 514/220; 514/468; 514/548

[58] Field of Search .................... 514/219, 220, 514/468, 548

[56] References Cited

U.S. PATENT DOCUMENTS

| 4,183,912 | 1/1980 | Rosenthale | 424/45 |
| 4,571,407 | 2/1986 | Chatterjee et al. | 514/464 |
| 4,582,824 | 4/1986 | Nishikawa et al. | 514/77 |
| 4,595,693 | 6/1986 | Biftu et al. | 514/461 |
| 4,621,083 | 11/1986 | Casals-Stenzel et al. | 514/220 |
| 4,734,280 | 3/1988 | Braquet | 424/195 |
| 4,900,729 | 2/1990 | Stransky et al. | 514/220 |
| 5,147,864 | 9/1992 | Wissner et al. | 514/82 |
| 5,202,313 | 4/1993 | Bombardelli et al. | 514/100 |
| 5,334,592 | 8/1994 | Billah | 514/220 |
| 5,346,894 | 9/1994 | Korth | 514/220 |
| 5,356,791 | 10/1994 | Korth | 514/220 |
| 5,399,348 | 3/1995 | Schwabe | 424/195.1 |

FOREIGN PATENT DOCUMENTS

| 869 136 | 1/1979 | Belgium . |
| 902 874 | 11/1985 | Belgium . |
| 0 151 687 | 8/1985 | European Pat. Off. . |
| 0 176 927 A2 | 4/1986 | European Pat. Off. . |
| 0 194 416 B1 | 9/1986 | European Pat. Off. . |
| 0 230 942 B1 | 8/1987 | European Pat. Off. . |
| 0 254 245 | 1/1988 | European Pat. Off. . |
| 0 255 028 A3 | 2/1988 | European Pat. Off. . |
| 0 256 687 A1 | 2/1988 | European Pat. Off. . |
| 0 312 913 B1 | 4/1989 | European Pat. Off. . |
| 0 459 432 A1 | 12/1991 | European Pat. Off. . |
| 0 540 767 A1 | 5/1993 | European Pat. Off. . |
| 0 431 535 | 3/1994 | European Pat. Off. . |
| 0 604 830 A2 | 7/1994 | European Pat. Off. . |
| 2 622 448 | 5/1989 | France . |
| 28 30 782 | 1/1980 | Germany . |
| 34 35 973 A1 | 4/1986 | Germany . |
| 35 02 392 A1 | 7/1986 | Germany . |
| 37 35 524 A1 | 4/1988 | Germany . |
| 37 10 921 A1 | 7/1988 | Germany . |
| 37 35 525 | 5/1989 | Germany . |
| 37 35 525 A1 | 5/1989 | Germany . |
| 39 40 091 | 12/1989 | Germany . |
| 0 459 432 A1 | 12/1991 | Germany . |
| 40 17 818 A1 | 12/1991 | Germany . |
| 40 34 090 A1 | 4/1992 | Germany . |
| 87 16 004 | 4/1992 | Germany . |
| 42 44 265 | 6/1994 | Germany . |
| 87/5890 | 9/1985 | Spain . |
| 2 162 062 | 1/1986 | United Kingdom . |
| WO 90/13299 | 11/1990 | WIPO . |

*Primary Examiner*—Kimberly Jordan
*Attorney, Agent, or Firm*—Nikaido Marmelstein Murray & Oram, LLP

[57] ABSTRACT

The invention refers to the composition of substances to prevent and treat endothelial cell-mediated disorders with pathological differentiation of endothelial cells, for example, in response to insulin, lipids, lipoproteins or LA-paf. The invention refers to simple methods to test and use antagonists against LA-paf, paf and very high affinity receptors on endothelial cells which can also be cultured on soluble particles for screening procedures. According to the invention genes producing very high affinity receptors, for example, in response to growth factors such as insulin. These genes can be transferred from adherent endothelial cell lines to soluble cells using standard procedures. Antagonists against LA-paf, paf and very high affinity receptors are administered by preference to healthy persons having risk factors to protect against aging and metabolic, genetic, chronicle, idiopathic, inflammatory or degenerative disorders. The antagonists can be administered by preference with food or topically, for example, with beauty products.

11 Claims, 2 Drawing Sheets

TREATMENT AND PREVENTION OF DISORDERS MEDIATED BY LA-PAF OR ENDOTHELIAL CELLS

CROSS-REFERENCES TO RELATED APPLICATIONS

This application is a continuation of U.S. patent application Ser. No. 08,444,103, filed May 18, 1995, now abandoned, which is a Continuation-In-Part of U.S. patent application Ser. No. 08/172,234, filed Dec. 23, 1993, now U.S. Pat. No. 5,530,023, which is a Continuation-In-Part of U.S. patent application Ser. No. 07/994,752, filed Dec. 22, 1992, now abandoned. U.S. patent application Ser. No. 08/172,234 is also a Continuation-In-Part of U.S. patent application Ser. No. 07/845,088, filed Mar. 3, 1992, now U.S. Pat. No. 5,356,791, which is a Divisional Application of Ser. No. 07/704,554, filed May 23, 1991, now abandoned. The present application is a Continuation-In-Part of the U.S. patent application Ser. No. 08/104,599, filed Aug. 11, 1993, now U.S. Pat. No. 5,480,881, which is a Continuation of the U.S. patent application Ser. No. 07/844,882, filed Mar. 3, 1992, now abandoned. This application is also a Continuation-In-Part of U.S. application Ser. No. 08/261,765, filed Jun. 17, 1994, now U.S. Pat. No. 5,605,927, which is a Continuation-In-Part of U.S. patent application Ser. No. 07/969,674, filed Oct. 28, 1992, now U.S. Pat. No. 5,346,894, and U.S. patent application Ser. No. 07/968,878, filed Oct. 30, 1992, now abandoned. This application is also a Continuation-In-Part of U.S. patent application Ser. No. 08/246,476, filed May 19, 1994, now U.S. Pat. No. 5,696,114, now U.S. Pat. No. 5,696,114, which is a Continuation of U.S. patent application Ser. No. 07/968,878, filed Oct. 30, 1992, now abandoned.

BACKGROUND OF THE INVENTION

The invention refers to the use of antagonists against LA-paf and novel very high affinity receptors on endothelial cells. According to the invention, endothelial cells express very high affinity receptors for paf, LA-paf and/or lipoproteins during their differentiation. Specific antagonists against very high affinity receptors, by preference on endothelial cells are tested using novel screening procedures to identify agents which may be clinically useful against endothelial cell-mediated diseases. According to the invention very high affinity receptors, by preference on endothelial cells, are involved with the transport of LA-paf and/or lipoproteins. LA-paf antagonists and antagonists against very high affinity receptors are used to treat or prevent recruitment of lipids. The undesirable side effects of lipid recruitment, pathological differentiation, irritation, aging or death of cells are thereby avoided. Antagonists can be administered by preference with food or beauty products to individuals requiring said substances. The invention successfully tests antagonists against LA-paf or very high affinity receptors on endothelial cells using novel methods.

The invention is based on novel methods based on several discoveries of the inventor. Very high affinity receptors on freshly prepared endothelial cells are compared here with receptors produced during differentiation of endothelial cell lines in response to growth factors such as insulin. The novel very high affinity receptors interfere with the inflow of lipid mediators to be enriched in the subendothelium. Thus, antagonists provide protection against fluid escape. Lowering of the endothelium barrier by pathological differentiation leads to cell emigration and/or edema formation with increased thickness of the basal lamina. Bacterial, cerebral, genetic, metabolic, inflammatory and allergic diseases can result from lowering the endothelial cell barrier with further adherence and/or emigration of blood cells to be prevented by antagonists against very high affinity receptors on endothelial cells.

Moreover, the inventor found out that LA-paf and lipoproteins constitute vehicles to transport lipids through the endothelium to the subendothelium mediated by an intermediate of very high affinity receptors. Cells such as platelets, monocytes or endothelial cells produce and release LA-paf which is associated with lipoproteins in the plasma. LA-paf is produced only in cells and is related to phospholipid metabolism, for example, during peroxidation. Thus, very high affinity receptors interfere either with lipoprotein transport through the endothelial monolayer or with emigration of activated blood cells such as monocytes which produce LA-paf and carry LA-paf from inside the vessels out.

LA-paf is an ether phospholipid which is physicochemically and functionally distinct as compared with chemically defined paf. The priority document of the present invention discloses at least two binding sites for LA-paf, with one binding site being accessible only for lipoproteins (normal or modified) and LA-paf |U.S. patent application Ser. No. 08/104,599|.

LA-paf is a preformed mediator present in healthy persons. According to the invention, LA-paf is a novel risk factor in metabolic and genetic diseases. This theory is based on the following findings: 1) Cells involved in atherosclerosis such as platelets, endothelial cells or monocyte/macrophage like cells synthesize LA-paf; 2) the atherogenetic low density lipoprotein (LDL) and cholesterol cause expression of specific paf binding sites on monocyte/macrophage like cells carrying LA-paf from inside the vessels out 3) lipoproteins contain LA-paf with a common binding site, for example, on platelets and 4) very high affinity receptors on endothelial cells interfere with the lipoprotein transport from inside the vessels out. This is shown here and in the priority documents |R. Korth, U.S. patent application Ser. No. 07/994,752 and European Patent, Publication No. 0312 913 B1 with the priority document P 37 35 525.2, Germany].

Based on these discoveries, the invention discloses novel methods to find antagonists against LA-paf or very high affinity receptors. Endothelial cells express "very high affinity receptors", as compared with tenfold lower affinity "high affinity paf receptors" on blood cells, cancer cells or cell lines. Endothelial cells and blood cells express distinct receptors on their surface which are antagonized by distinct and specific antagonists. Immortalized endothelial cell lines, for example, express very high affinity receptors during their differentiation. Antagonists against various receptors for paf, lyso paf, lipoproteins or LA-paf can be tested on the surface or inside of cells.

Based on these findings antagonists are administered to persons with indicated risk factors to maintain the integrity of both the endothelium and the subendothelium and to prevent and treat diseases as mentioned. Very high affinity receptors on endothelial cells are blocked by antagonists to inhibit the binding of LA-paf, paf, blood cells and/or lipoproteins and to reduce the transport of pathological compounds, for instance lipids, through the endothelium. Antagonists against very high affinity receptors by preference on endothelial cells are not defined prior to the present invention. Simple methods select antagonists against LA-paf receptors, paf metabolism and LA-paf production using preferably platelets, neutrophils, eosinophils, lymphocytes, monocytes, tissue cells including adipocytes, or cell lines. The methods and their use are fully described here and in the priority documents of the present invention [U.S. patent application Ser. No. 08/104,599, European Patent Application, Publication No. 0 459 432 A1].

Antagonists

Substances that antagonize very high affinity receptors or LA-paf can be selected from the group consisting of triazolothieno-diazepines or analogs, as well as homologous compounds. In addition ginkgolides and paf analogues, such as CV 3988, are suitable. Triazolothieno-diazepines and ginkgolides are paf antagonists as described [R. Korth (1989) Brit. J. Pharmacol. 98, 653–661; R. Korth (1988) Eur. J. Pharmacol. 152, 101–110]. Of the triazolothieno-diazepine compounds WEB 2086 and WEB 2098 are especially suitable. Of the ginkgolides BN 52020, BN 52021 and a mixture of BN 52020, BN 52021 and BN 52022, which is referred to as BN 52063, achieve the best results. The synthetic compound BN 50739 [T. Yue et al., J. Exp. Pharmacol. Exp. Therapeutics 257, 1991, pp 374–381] is used here as an example for synthetic ginkgolides because it contains the active chemical structures of both ginkgolides and hetrazepines. The chemical term of CV 3988 is rac-3-(N-n-octadecyl carbamoyl oxy)-2-methoxypropyl 2-tiazolioethyl phosphate; the term of WEB 2086 is 3-(4-(2-chlorophenyl)-9-methyl-6H-thieno(3,2-f) (1,2,4)triazolo-(4,3-a)-(1,4) diazepine-2yl)-1-(4-morpholinyl)-1-propanone; the term of WEB 2098 is (3-(4-(2-chlorophenyl)-9-cyclopropyl-6H-thieno(3,2-f)-(1,2,4) triazolo-(4,3-a)(1,4)diazepine-2yl)-1-(4-morpholinyl)-1-propanone; the term of BN 52020 is 9H-1, 7a-Epoxymethano)-1H, 6aH-cyclopenta(c)furo(2,3-b)furo (3',2':3,4) cyclopenta(1,2-d)furan-5,9,12(4H)-trione, 3-tert-butylhexahydro-4, 7b-dihydroxy-8-methyl; the term of BN 52021 is 9H-1, 7a-Epoxymethano)-1H,6aH-cyclopenta(c) furo(2,3-b)furo-(3',2':3,4) cyclopenta(1,2-d)furan-5,9,12 (4H)-trione, 3 tert-butylhexahydro-4, 4b-11-trihydroxy-8-methyl; and the term of BN 52022 is 9H-1, 7a-(Epoxymethano)-1H, 6aH-cyclo-penta(c)furo(3',2':3,4) cyclopenta (1,2-d)furan-5,9,12(4H)-trione, 3 tert-butyl hexahydro-2,4,7b,11-tetrahydroxy-8-methyl. The chemical term of BN 50739 is tetrahydro-4,7,8,10methyl(chloro-2 phenyl)6(dimethoxy-3,4-phenyl)thio) methylthiocarbonyl-9pyrido(4',3'-4, 5)thieno(3,2-f)triazolo-1,2,4(4,3-a) diazepine-1,4).

The antagonists can be administered topically, orally, parenterally, by liposomes, food, beauty products, syrups or inhalation. According to the invention paf or LA-paf antagonists can also be administered in form of food for example with "FIDA infants' foods for invalids and seniors" [R. Korth U.S. Trademark Application, Ser. No. 74/416,579]. The compounds are administered as active ingredients in conventional pharmaceutical preparations, e.g. in compositions comprising an inert pharmaceutical vehicle and an effective dose of the active substance, such as tablets, coated tablets, capsules, lozenges, powders, solutions, suspensions, aerosols for inhalation, ointments, emulsions, syrups, food, suppositories, etc.

An emulsion has been prepared containing ginkgolides for topical use adding a commercially available ginkgolide solution (Tebonin forte, Schwabe, Karlsruhe, Germany) to commercially available "pH-5 Eucerin Intensivlotio" (Beiersdorf, Hamburg, Germany), for example 30 gtt ad 125.0 ml. Ginkgolides can also be added to food. Triazolothieno-diazepines, preferably lipophilic compounds, can be used as well. An effective dosage of the agents according to the invention is preferably between 0.01 and 50 mg. For oral administration, between 3 and 20 mg/kg are used. For intravenous or intramuscular administration, between 0.01 and 50 mg, or between 0.1 and 10 mg/kg are used. For inhalation, solutions should be used containing, for example, 0.01 to 1.0% of the agent.

BN 50739 has been administered to endotoxin-treated rabbits (3 and 10 mg/kg i.p., IHG, Le Plessis Robinson, France in Yue et al., J. Pharmacology and Experimental Therapeutics 254, May 1990, pp. 976–981). Stransky et al. describe novel Thieno-1,4-Diazepines (U.S. Pat. No. 4,900, 729) with doses up to 200 mg/kg p.o. using guinea pigs.

According to the invention natural Ginkgo biloba is administered for the first time by food for example "FIDA-infants' foods for invalids and seniors" against irritation, pathological differentiation, irritation, aging, degeneration and death of cells in vivo. The administration of ginkgolides, preferably with food, is suitable for example for older persons and children. The invention is suitable to compose and produce FIDA-infants' foods for invalids and seniors.

Beauty products can be tested and produced for their clinical use to create new vessels and to prevent and treat aging, edema formation as well as immunological, genetic or metabolic disorders. Beauty products are administered, for example, topically using pharmaceutical vehicles by preference with acid pH values.

Clinical use

A clinical relevance of the invention is shown because LA-paf can be considered as a novel risk factor. Freshly prepared endothelial cells express very high affinity receptors and LA-paf is present in human cells and lipoproteins. According to the invention, specific antagonists against LA-paf and very high affinity receptors can be used for protection of the endothelial barrier in vivo. They are specifically useful to enhance by preference the creation of new vessels and/or to treat and prevent pathological water osmoregulation with irritation of the tissue, for example, the lymphatic system, neuronal cells, the brain, the skin, the kidney, and the heart prematurely growing old. They protect against an increased thickness of the basal lamina and/or the subendothelial tissue. This protects, for example, in cases of diabetes, against blindness or kidney diseases. The cause of diabetes cannot yet be treated, but persons with risk factors such as hyperglycemia, obesity, hyperinsulinemia, acid pH values and/or hyperlipidemia can be treated as long as they are healthy, to protect their tissue, particularly their vascular system, their eyes, their heart and their kidneys. Antagonists prevent edema formation, pathological irritation, differentiation, aging and death of cells. Pathological differentiation of endothelial cells, caused preferably by insulin, cholesterol, lipoproteins (normal or modified) or acid pH values has a considerable importance in metabolic, addictive, inflammatory, allergic, vascular, chronicle, idiopathic, genetic diseases and transplantation. Protection of healthy endothelial cells by creation of new vessels can be mediated by administration of compounds of the invention, by preference with food and beauty products.

Antagonists with an effect on the central nervous system protect either the endothelial blood brain barrier via an intermediate of cell adherence, or emigration and/or neuronal cells. Endothelial cells produce here lyso paf, and lyso paf is a novel neurotransmitter interacting with specific lyso paf receptors on neutrophils and/or neuronal cells in the priority document of the present invention [R. Korth, U.S. patent application Ser. No. 08/261,765]. Antagonists against chronic endothelial cell irritation with production of lyso paf and/or activation of the protein kinase C protect, for example, against neoplastic, mental, neuronal or inflammatory diseases.

Water intoxication has been shown to be a serious problem in many patients with chronic disorders. For example, seniors, diabetics or psychiatric patients have polydipsia and hyponatremia with unexplained defects in urinary dilution, osmoregulation of water intake and vasopressin secretion [M. B. Goldman et al. (1990) New Engl. J. Med. 318, pp 397–403]. Medicaments containing bilobalid are used to treat nervous diseases [I. Anadere et al. (1985) Clinical Hemorheology 5, pp 411–420], but ginkgolides protect here, for the first time, healthy endothelial blood brain barrier to prevent and antagonize episodic defects in osmoregulation.

The increase of prostacyclin in response to antagonists against endothelial very high affinity receptors is a novelty and proposes a novel clinical use. Indicated antagonists are clinically used to protect the vascular system and/or to trigger the synthesis and release of prostacyclin, for example, during administration of prostaglandin antagonists such as aspirin.

The tumor promoting factor PMA which has considerable importance in cancer causes expression of paf receptors on non-differentiated cells [R. Korth et al., Chem. Phys. Lipids 70 (1994) 109–119]. Thus, the selected compounds might also protect against cancer disease or metastasis.

Leukocytes such as neutrophils, eosinophils, monocytes or lymphocytes are involved in various inflammatory reactions such as allergy, cell adherence and migration, as well as bacterial or fungal phagocytosis. Novel antagonists inhibit [$^3$H]paf binding and cellular functions such as calcium flux. Novel binding assays demonstrate the differences between paf receptors on the surface of intact cells. For example, intact human platelets, blood neutrophils and eosinophils have different paf, LA-paf and lyso paf receptors determined with binding assays using unlabelled paf, LA-paf or lyso paf (500 nM) with or without specific paf, lyso paf and LA-paf antagonist. These antagonists are by preference ginkgolides or triazolothieno-diazepines. A $K_d$ value of 0.44 nM with 3612 high affinity (ha) receptors per neutrophil, a $K_d$ value of 9.2 nM with 4100 lyso paf receptors per neutrophil and a $K_d$ value of 5.5 nM with $8.6 \times 10^4$ moderate affinity (ma) receptors per eosinophil are calculated using Scatchard plot analysis of the saturated specific binding. LDL, cholesterol and Lapaf significantly upregulated these receptors on platelets with paf and lyso paf upregulation of neutrophils and low dose paf (not lyso paf) downregulation of eosinophil receptors. Intact neutrophils, monocytes and endothelial cells, but not platelets and eosinophils metabolize added paf and all these cells produce and carry LA-paf. These experiments are fully described in the priority documents (U.S. patent application Ser. Nos. 08/104,599; 08/261,765; 08/246,476 and 08/172,234).

According to the invention, novel methods are used to select specific antagonists against high, very high or moderate affinity sites for paf, lipoproteins, LA-paf and/or lyso paf on various cells. Clinically the selected compounds are used for the prevention and treatment of genetic diseases by preference of risk factors such as obesity, hyperlipidemia with or without arteriosclerosis, for neuronal, cerebral, mental, psychotic diseases. The novel compounds are administered to treat and prevent vascular and skin diseases with oedema formation or metabolic disorders. They reduce side effects of drugs such as glucocorticosteroids, cAMP modulating drugs, antihistamines and prostaglandin antagonists. Leukocyte-, lipoprotein-, and/or endothelial cell-mediated diseases are involved in degenerative, allergic, cancer and inflammatory disorders to be treated with compounds selected as described (U.S. patent application Ser. Nos. 08/104,599; 08/261,765; 08/246,476 and 08/172,234).

Novel Methods

The present invention discloses novel methods to test the efficacy of antagonists using, for example, endothelial cell lines. Differentiated cells are compared with non-differentiated endothelial cell lines such as immortalized endothelial cells, for example, umbilical vein endothelial cells (Im-Huvec). This invention also discloses quick and simple methods of endothelium differentiation with various factors such as growth factors, such as insulin.

According to the invention, endothelial cells express very high affinity (vha) receptors during differentiation as compared with nearly no receptors on non-differentiated cells, such as Im-Huvec cells see Example 1. Freshly prepared endothelial cells express in vivo, very high affinity receptors as shown in Example 2. According to the invention very high affinity receptors interfere with the binding and metabolism of paf and LA-paf in endothelial cells, platelets and monocyte/macrophage like cells. See Examples 3 and 4 and the priority document [U.S. patent application Ser. No. 08/104,599]. Thus, antagonists are selected with novel methods which are fully described in the examples to successfully inhibit very high affinity receptors, LA-paf binding, LA-paf effects and/or production.

According to the invention, gene transfer of differentiated endothelial cells into soluble cells is proposed using a standard procedure described for high affinity paf receptors from guinea pig lungs and blood cells [Z. Honda et al. (1991) Nature 349, 342–346]. The invention discloses a procedure to test antagonists of very high affinity paf receptors on soluble cells or endothelial cells cultured, for example, on soluble particles.

In the case that endothelial cells are used, the procedure of the present invention can be used to determine the activity of specific paf or LA-paf antagonists. According to the invention, endothelial cells, for example, freshly prepared or immortalized endothelial cells after differentiation, are used to test the efficacy and specificity of antagonists. In order to conduct a quick and simple test on the efficacy with regard to their antagonistic activity vis-a-vis paf or LA-paf receptors, i.e. to use a screening procedure, for example, to find effective antagonists which can then be taken into consideration for treating or preventing disorders caused by pathological irritation, differentiation, aging or death of cells, then according to the invention, the best method is to proceed as follows.

a) Endothelial cells are cultured or non-differentiated endothelial cells are mixed in culture with at least one compound of various differentiation factors, for example, lipids, (lipo)proteins, LA-paf, hormones such as steroids, for example, cholesterol, growth factors such as insulin or erythropoietin etc., inflammatory mediators such as LA-paf or cytokines, compounds such as PMA or DMSO and acid medium, b) a given quantity of purified cells is mixed with a given quantity of labelled paf or LA-paf and the antagonist to be determined, c) a given quantity of the same purified cells is mixed with a given quantity of labelled paf or LA-paf in the absence of antagonists, d) the cells are separated from the mixtures b) and c) in each case, e) the quantity of labelled paf or LA-paf bound to the cells is measured in each case, and f) the efficacy of the paf or LA-paf antagonist is determined from the relationship between the quantity of labelled paf or LA-paf which is bound to the cells according to b) in the presence of the antagonist on one hand, and the quantity of labelled paf or LA-paf which is bound to the cells according to c) in the absence of the antagonist on the other hand.

Preferably human umbilical vein endothelial cells (Huvec) or non-differentiated endothelial cells, for example, immortalized cells (Im-Huvec) after differentiation, are used for the procedure. It is also suitable to use venous or arterial endothelial cells from human or animal tissues. The method of the invention determines the efficacy of LA-paf antagonists or antagonists specifically directed against very high affinity receptors on endothelial cells. Other cells such as platelets, neutrophils, eosinophils, lymphocytes, monocytes, tissue cells including adipocytes and cell lines such as monocyte-macrophage like cells, are also used to test antagonists or to produce LA-paf.

Differentiation of cell lines, for example, of Im-Huvec can be performed by non-specific cell stimulation. Cells can be treated, for example, with growth factors, lipids, steroids hormones and inflammatory mediators such as cholesterol, LDL, LA-paf, insulin, or cytokines. Infection, activation of the protein kinase C, and acid medium cause expression of the indicated receptors. Cells can be treated during a shorter incubation period with acid pH values and PMA, for example, to activate the protein kinase C. Cell lines such as U 937 cells express paf receptors during bacterial or fungal infection. The invention is suitable to select specific antagonists (and antibodies) for a clinical use against the pathogenesis of metabolic, genetic, inflammatory and/or neoplastic disorders.

The ligand of binding studies according to step c) d) e) f) can be paf or LA-paf, their analogues, and antagonists with analogues or antibodies in a marked, fluorescent or colored form. As labelled ligands agonists, antagonists or antibodies can be used with and without labelled and unlabelled, colored or fluorescence labelled paf, LA-paf with analogues, antibodies and antagonists.

The mixing according to the steps b) and c) is done preferably at a temperature of 20° C. or 4° C. After mixing, the cells are incubated for 30 min to several hours, or, overnight, before they are separated according to step d) of the procedure of the present invention. Endothelial cells are preferably washed with acid buffer and detached after the binding procedure in a cool medium with EDTA and without Magnesium and Calcium. It is known that the cells are preferably separated from the buffer by centrifugation or filtration. The separation of the cells according to step d) can be performed by filtration or centrifugation. After this, the quantity of labelled paf or LA-paf which is (specifically) bound to the cells is determined. If radioactively labelled paf or LA-paf are used, only the radioactivity bound to cells is measured. The radioactivity bound in the filter without cells is subtracted from these values.

By drawing calibration graphs, which are obtained with varying quantities of the antagonist in accordance with step b), it is thus possible to obtain the efficacy of the antagonist at a 50% inhibitory value, i.e. as that quantity of the antagonist which, in relation to a given quantity of cells, leads to a 50% inhibition of the reversible binding of the labelled ligand. It is also possible to calculate binding kinetics of antagonists.

Antibodies, by preference monoclonal antibodies, against LA-paf itself or paf receptors can be formed for diagnostic tests or the prevention and treatment of diseases. According to the invention antibodies can be tested or produced using soluble cells, for example, antibodies with agonist and antagonist potency using radio- and fluorescence labelled or colored compounds. The difference between differentiated vs. non-differentiated cells with presence and absence of paf or LA-paf receptors can be used to produce antibodies using standard procedures. Antibodies against surface proteins of non-differentiated cells are subtracted from those on differentiated cells using screening procedures according to the invention. The invention refers also to production of LA-paf in large amounts which is an essential condition for production of antibodies or of enzyme assays. Antibodies, for example, against lipoproteins are used successfully in the priority document [U.S. patent application Ser. No. 08/104, 599, FIG. 5].

Diagnostic tests for the clinical use can be facilitated using special testing containers which are commercial available and which are modified for smaller blood volumes as proposed in German utility model application G 87 16 004.8.

Since the specific binding of paf, LA-paf and analogues is in close correlation with the cellular signal transduction and cellular calcium stream, the procedure of the present invention can also be used for measuring paf, LA-paf and agonists, for example, by comparing their effects on the cellular calcium stream with calibration graphs of synthetic paf or mediator production and release as described [R. Korth (1989) Brit. J. Pharmacol. 98, 653–661].

By preference endothelial cells cultured on dishes or on soluble particles but also soluble cells, for example, cell lines, fungal cells, cancer cells or bacterial cells are used, by preference after gene transfer. These cells express distinct receptors for paf, LA-paf, lipoproteins, lyso paf and paf analogues to select distinct antagonists.

In order to perform a simple procedure to test antagonists preferably against very high affinity receptors on endothelial cells genes can be enriched, defined and transferred, for example, into soluble cells, by preference cell lines and bacterial cells. The invention refers to transfer, by preference genes interfering with very high affinity receptors or LA-paf production to soluble cells. Next, screening procedures can be performed preferably by automatons. The antagonists can be tested according to the following procedure:

a) Endothelial cells are cultured, b) endothelial cells are mixed with at least one differentiation factor producing endothelial receptors for example the growth factor insulin, c) endothelial cells are preferably washed with acid pH values and binding studies with paf, LA-paf, analogues of paf, antagonists or antibodies are performed as described above and according to step b) and c) treated endothelial cells are compared with non-treated cells in the presence and absence of labelled and unlabelled agonists, antibodies and antagonists, d) genes producing endothelial receptors for paf or LA-paf according to b) and c) are transferred into soluble cells for example cell lines, cancer cells, fungal cells or bacterial cells using standard procedures or endothelial cells are cultured on soluble particles, e) soluble cells and/or soluble particles with endothelial cells expressing very high affinity receptors are used to test substances, for example, specifically related against high, very high or moderate affinity receptors for paf, LA-paf with analogues or lipoproteins using by preference screening procedures with automatons.

The culture of endothelial cells, for example, Huvec or endothelial cell lines, for example, Im-Huvec can be performed preferably with standard culture techniques. The endothelial cells, for example immortalized endothelial cells, can be cultured also on soluble particles to further facilitate the procedure. The culture dishes and soluble particles can also be mixed for example with gelatin and growth factors, hormones, mediators, lipids and antagonists. Endothelial cells can also be grown on smooth muscle cells to define and treat cellular interactions leading to vascular regulation. In this context, functional assays can be used, for example, cell adherence, calcium influx or production and release of mediators in the absence and presence of antagonists and antibodies. According to the invention binding studies are performed with unlabelled and/or labelled agonists, antagonists, antibodies, hormones, lipids or (lipo) proteins as described above. The expression of genes for paf or LA-paf receptors, for example, in response to insulin the binding studies according to b) and c) can be defined and enriched, for example, during culture (2 to 24 h) in the presence of 2 I.E. human insulin. Other growth factors and compounds can be added to a standard medium. Compounds including pharmacological substances can be added to antagonize the production and expression of genes encoding paf or LA-paf receptors as well as LA-paf production.

It is suitable to use soluble cells instead of adherent cells to facilitate screening procedures of new compounds according to e). The compounds are, for example, antibodies and antagonists directed by preference against very high affinity paf receptors for LA-paf, lipoproteins or paf. Alternatively endothelial cells can be cultured on soluble particles. The latter possibility is also suitable because various cellular transduction mechanisms might define the structure of novel receptor protein(s). Genes might produce very high affinity receptors, paf and/or LA-paf receptor(s) by preference with different cell-specific structures but also phosphorylation and/or modulating proteins etc. might be expressed during differentiation.

Antagonists inhibit either receptor-dependent interactions and metabolism of paf and LA-paf or LA-paf production. According to the invention, LA-paf is produced during oxidation of long chain fatty acid derivatives such as the cellular paf metabolite alkyl-acyl-glyceryl-phosphorylcholine. Oxidation of long chain fatty acid paf metabolites triggers LA-paf production to be used or to compose, for example, food containing antioxidant substances such as vitamins. Lipoproteins are used here for the first time as growth factors to differentiate cells with expression of paf receptors. This interferes with the cellular transport of lipoproteins and/or LA-paf from inside the vessels out. Lipoproteins bind directly to very high affinity receptors on the endothelium with or without intermediate of peroxidation.

The invention refers to in vitro production of LA-paf by cell lines. Cellular LA-paf production is a quick and simple method to produce large quantities of labelled and unlabelled LA-paf, for example, to perform binding studies with labelled and/or unlabelled LA-paf or to produce antibodies as described above. The invention is also suitable to test and produce food and beauty products interfering, by preference with peroxidation and LA-paf production. When cell lines are used to produce labelled or unlabelled LA-paf then according to the invention, the best method is to proceed as follows:

a) cell lines are cultured in the presence of serum;

b) labelled or unlabelled paf or analogues are added;

c) cells are extracted using standard procedures for phospholipid extraction.

According to a) the cell lines are by preference monocytemacrophage like cells. Blood and tissue cells, cancer cells bacterial as well as fungal cells can be used in vivo and in vitro using all culture techniques.

According to b) lipids, oxidized phospholipids, ether phospholipids, labelled or unlabelled paf or LA-paf with analogues can be added which are metabolized by cell lines. Resident blood cells as well as monocyte/macrophage like cells produce and carry unlabelled LA-paf without addition of paf.

According to c) all procedures of phospholipid extraction and/or purification can be used by preference HPLC with a biological assay to quantify and purify labelled or unlabelled LA-paf.

EXAMPLE 1

Specific Antagonists and cell lines

The first example provides a novel method to test antagonists using endothelial cell lines.

1.1. Culture of endothelial cells

Endothelial cells, for example, umbilical endothelial cells (Im-Huvec) were immortalized to be characterized as endothelial cells as described [Llorens Cortes et al. (1992) J. Biol. Chem. 267, 14012–14018]. Cells were cultured by preference in a M199 medium containing 25 mM Hepes and 2 g/l NaHCO$_3$, 10% heat-inactivated foetal calf serum, 1% amino acids, 1% folic acid, 1% RPMI vitamins, 0.1% gentamicin and 4 mM glutamine (Gibco, Paisley, Scotland). The cells were incubated in 75 cm$^2$ culture flask on 0.2% gelatine with media changes every 2–3 days. When cultures reached confluence (3–5 days), the cells were harvested by brief exposure to trypsin-EDTA and plated into culture dishes coated with 0.2% gelatin at 1:3 split ratio. Endothelial cells were grown thereafter, for example, 5 days with or without addition of human insulin (2 I.U. per 5 ml medium, 20 h).

1.2. Binding studies with [$^3$H]paf

Immortalized endothelial cells (Im-Huvec) were tested as an example because the number of endothelial cells prepared freshly from one umbilical vein cord is limited. Im-Huvec were incubated with [$^3$H]paf (100–600 pM, 0.25% BSA, 30 min at 20° C.) and specific [$^3$H]paf binding was assessed in the absence and presence of 50 nM paf. Im-Huvec were cultured before 20 h in a medium with or without addition of human insulin (2 I.U. per 5 ml, Hoechst, Germany) before three washes. After the binding procedure free radioactivity was washed twice from the confluent monolayer with Tyrode's buffer (pH 6.4) containing BSA and then once with cold isotonic NaCl-EDTA (5 mM) solution. Cells were detached by incubation in the latter medium keeping the dishes on ice for at least 30 min. Detached cells were separated from the medium by vacuum filtration onto GF/C filters in a Millipore vacuum system. Incubation and washing buffers as well as control buffers were filtered to recover cells detached during the washing procedures. Filters were washed twice with cold Tyrode's buffer and the radioactivity of the filter-bound endothelial cells was counted under standard conditions in scintillation fluid. Filter-bound radioactivity without endothelial cells was subtracted from filter-bound radioactivity with endothelial cells. Added [$^3$H]paf was expressed in pM and bound [$^3$H]paf in fmol per dish of adherent, confluent endothelial cells (fmol/ml).

1.3. Results

Figure 1:
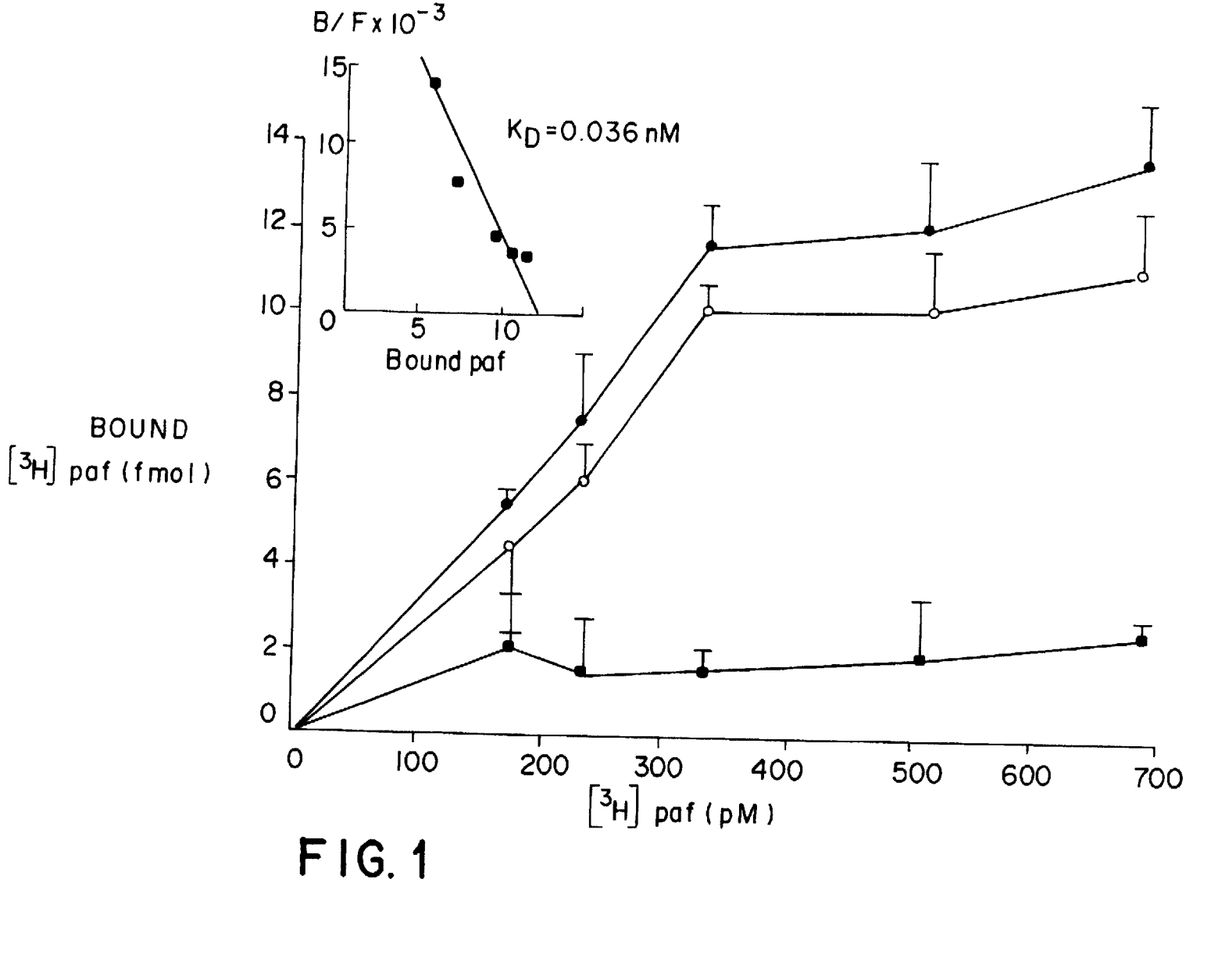
FIG. 1 shows the paf binding data using an endothelial cell line, for example, Im-Huvec.

According to the invention Im-Huvec were cultured in the presence of insulin. Paf binding studies were performed to calculate the binding kinetics of endothelial receptors with Scatchard plot analysis of the specific and saturated [$^3$H]paf binding (FIG. 1). The $K_D$-value was tenfold lower using differentiated Im-Huvec indicating a novel very high affinity receptor on endothelial cells as compared with differentiated monocyte/macrophage like cells in the priority document (U.S. patent application Ser. No. 08/104,599). In these experiments unlabelled paf was used as unlabelled ligand (50 nM, 0.25% BSA, 20° C., 30 min, FIG. 1). In contrast, no specific [$^3$H]paf binding was detected when Im-Huvec were cultured without addition of human insulin indicating expression and/or production of novel receptors on endothelial cells during differentiation.

We investigated here firstly the specific binding of [$^3$H]paf (690 pM) to Im-Huvec with or without insulin (20 h, 0.4 I.U.×ml$^{-1}$). Insulin mediated specific [$^3$H]paf binding to Im-Huvec as compared with non-specific [$^3$H]paf binding to non-treated cells. The total [$^3$H]paf binding to insulin-treated cells was 13.7±1.2 fmol and unlabelled paf decreased 2.6±0.2 fmol of the bound [$^3$H]paf. In contrast, unlabelled paf did not inhibit [$^3$H]paf binding to non-treated Im-Huvec (4.2±1.2 fmol vs. 6.5±1.0 fmol). The values represent means±1 S.D. of 3 experiments.

According to the invention, growth factors express very high affinity receptors on endothelial cells, for example, human insulin (2 I.E.) during a 20 h incubation period as compared with similar receptors on fresh endothelial cells in the priority document [U.S. patent application Ser. No. 07/994,752].

An antagonist, for example, BN 50739 (10 and 20 µM) do not modulate paf binding to non-treated Im-Huvec. However, according to the invention the antagonist BN 50739 (20 µM) reached specific paf binding of 5.8 fmol per culture dish of adherent confluent endothelial cells when Im-Huvec were cultured, for example, in the presence of insulin. According to the invention very high affinity receptors for paf, LA-paf or lipoproteins are inhibited by specific antagonists. The tested substances are also suitable to antagonize very high affinity receptors on endothelial cells after differentiation with insulin. Antagonists against very high affinity receptors protect the (sub)endothelium tissue against the endothelial transport of lipoproteins as LA-paf and lipoproteins share a common novel receptor.

1.4. Legend for FIG. 1

[$^3$H]paf binding to differentiated Im-Huvec (20° C., 30 min, 0.25% BSA). The total [$^3$H]paf binding (●) and the non-specific [$^3$H]paf binding (○) were determined in the absence or presence of 50 nM unlabelled paf to yield the saturated specific [$^3$H]paf binding (■). Values are expressed in fmol bound [$^3$H]paf to one confluent dish of Im-Huvec. They are means±1 S.D. of three distinct experiments.

Inset of FIG. 1: Scatchard plot analysis of specifically bound [$^3$H]paf (fmol) and bound/free (B/F, fmol B/pM). Values are means of three experiments shown in FIG. 1.

EXAMPLE 2

Human umbilical vein endothelial cells 2.1. Preparation and culture of endothelial cells Human endothelial cells were freshly isolated from umbilical cord veins as described [R. Korth et al. (1989) Brit. J. Pharmacol. 98, 653–661]. Briefly, the vein was cannulated and filled with 0.1% collagenase solution. After 10 min incubation at 37° C., the detached cells were flushed out and collected by centrifugation. Huvec were resuspended in Ham's F-12 medium with 10% heat-inactivated foetal calf serum, 1% Ultroser SF and supplemented with 90 µg×ml$^{-1}$ heparin, 50 U×ml$^{-1}$ penicillin and 50 µg×ml$^{-1}$ streptomycin. The cells were incubated in 25 cm$^2$ culture flask for 1 h. The non-adherent cells were then aspirated and the adherent cells were further cultured in fresh culture medium with media changes every 2 days. When cultures reached confluence (3–5 days), the cells were harvested by brief exposure to trypsin-EDTA and plated into 35 mm culture dishes at 1:3 to 1:5 split ratios. Huvec were grown thereafter in Ham's F-12 medium with 15% FCS, 1% Ultroser and 90 µg×ml$^{-1}$ heparin with medium changes every 2–3 days. Cells reached confluence after 4–6 days and their number per dish was assessed using preparations of nine distinct cord veins with a mean of 5.2±0.15×10$^5$ cell per dish (±1 S.E.M.). Huvec at first passage were used throughout this study, and were characterized as endothelial cells based on morphologic criteria and by indirect immunofluorescence using a specific antiserum to human Factor VIII antigen, a customary marker of endothelial cells. Cell preparations contained no monocyte/macrophage cells, as defined by morphologic criteria and by indirect immunofluorescence using a monoclonal antibody to alpha$_2$-macroglobulin.

2.2. Binding studies with [$^3$H]paf

[$^3$H]Paf binding studies were performed using adherent human umbilical vein endothelial cells at first passage throughout this study. Cells were washed three times with Tyrode's buffer (pH 6.4) containing 0.25% BSA without addition of Ca$^{2+}$ to remove culture medium. Next, [$^3$H]paf binding experiments were performed (pH 7.4; 1.3 mM Ca$^{2+}$) using paf or indicated paf receptor antagonists as unlabelled ligands, at 20° C. for an incubation period of 30 min or at 4° C. incubated for several hours, for example, overnight.

In a first set of experiments Huvec were cultured in a medium containing 10% (v/v) heat-inactivated calf serum. Washed Huvec were incubated at 20° C. with [$^3$H]paf (100 µl, 65 pM, final concentration) in the absence and presence of unlabelled paf (500 nM) in Tyrode's buffer (900 µl) for different time periods (3, 5, 15, 30 min). Next, different concentrations of [$^3$H]paf (32–650 pM, final concentrations) were incubated with Huvec in the absence or presence of unlabelled paf (500 nM) at 20° C. for 30 min as described above. The paf analogue CV 3988 (3, 10 and 30 µM, final concentrations), the paf receptor antagonists WEB 2086 (1, 10 and 1000 nM) or ginkgolides, for example, BN 52021(6, 10 and 60 µM) were added together with [$^3$H]paf (650 pM) for 30 min at 20° C. as compared with vehicles. Huvec were also incubated with [$^3$H]paf (650 pM) in the presence and absence of the paf-enantiomer or 0.1 mM lysine-aspirin.

In a second set of experiments Huvec were kept for 48 h in a medium containing 15% (v/v) serum substitute instead of heat-inactivated foetal calf serum to minimize a putative interference of plasma (lipo)proteins. In this context, [$^3$H]paf binding studies were performed at 4° C. (20 h) in order to avoid paf metabolism. Huvec were preincubated with the paf analogue CV 3988 (10 µM) or vehicle for 15 min and then incubated at 4° C. overnight in the presence of different [$^3$H]paf concentrations (160–650 pM).

After the binding procedure, free radioactivity was washed twice from the confluent monolayer with Tyrode's buffer (pH 6.4) containing BSA and then once with cold isotonic NaCl-EDTA (5 mM) solution. Cells were detached by incubation in the latter medium keeping the dishes on ice for at least 30 min. Detached cells were separated from the medium by vacuum filtration onto GF/C filters in a Millipore vacuum system. Incubation and washing buffers as well as control buffers were filtered to recover cells detached during the washing procedures. Filters were washed twice with 10 ml cold Tyrode's buffer and the radioactivity of the filter-bound endothelial cells was counted under standard conditions in scintillation fluid (BCS). Filter-bound radioactivity without endothelial cells was subtracted from filter-bound radioactivity in the presence of endothelial cells. [³H]Paf was calculated in fmol bound to an indicated number of adherent endothelial cells.

2.3. Results

Confluent Huvec bound [³H]paf time-dependently. Incubation of adherent endothelial cells with [³H]paf (65 pM) together with unlabelled paf (500 nM, 0.25% BSA) resulted in the reduction of total [³H]paf binding by 33.0±6.6% after 3 min incubation at 20° C. (mean±1 S.D., n=3).

Huvec bound [³H]paf (32–650 pM) in a concentration-dependent manner. The binding was partially reversible when [³H]paf was added together with unlabelled paf (500 nM, 30 min). Scatchard analysis showed for the first time very high affinity (vha) paf binding sites with a low $K_D$ value (0.04 or 0.15 nM) and a $B_{max}$ of 2.5 fmol indicating 2800 binding sites per adherent endothelial cell. The specific [³H]paf binding reached saturation indicating a constant amount of specific paf binding sites. The paf-enantiomer did not interfere with total [³H]paf binding (650 pM, 10.8 fmol vs. 10.3 fmol, one experiment representative of three).

The paf receptor antagonist WEB 2086 and the paf analogue CV 3988 (30 µM) decreased the total [³H]paf binding at 20° C. with a dose-dependent increase of specific [³H]paf binding (Table I). The paf receptor antagonist WEB 2086 reached inhibitory effects as compared with ginkgolides, for example BN 52021, or the paf-analogue CV 3988.

Next, paf binding studies were performed with Huvec at 4° C. after 48 h culture in a medium with serum substitute instead of heat-inactivated foetal calf serum. A paf receptor antagonist, for example, the paf analogue CV 3988 inhibited [³H]paf binding at 4° C. CV 3988 was added 15 min prior to [³H]paf reaching a maximal inhibitory effect of 2.4 fmol per $5.2±0.15×10^5$ cell at 325 pM added [³H]paf. Paf degradation was excluded at 4° C. (not shown). When endothelial cells were detached with trypsin instead of cold NaCl-EDTA [³H]paf binding was not inhibited by unlabelled paf (5.2 fmol vs. 5.2 fmol, one experiment representative of three).

Another set of control experiments was performed. Addition of lysine-aspirin did not inhibit but increased the binding of [³H]paf (325 pM, 7.5±1.5 fmol) as compared with vehicle (5.1±1.7 fmol, mean±1 S.D., n=6). Paf receptor antagonists, for example, WEB 2086, CV 3988 or the ginkgolide BN 52021, fully inhibited endothelial [³H]paf binding after addition of aspirin.

The stable metabolite 6-keto-PGF1-alpha increased in response to paf to be inhibited in the presence of the paf analogue CV 3988 (as described [R. Korth et al. (1989) Vascular Endothelium. Receptors and Transduction Mechanisms. Eds. J. D. Catravas et al., 89–98]. However, quite surprisingly 6-keto-PGF1-alpha increased from 127±3 pg per ml to 145±11 pg per ml in the presence of 100 nM WEB 2086 and from 50±2 pg per ml to 126±10 pg per ml in the presence of the ginkgolide BN 52021 as compared with vehicles (means±1 S.D., n=3). Thus, specific antagonists directed against very high affinity receptors on endothelial cells increase here for the first time the prostacyclin release to support their clinical use. Antagonists against very high affinity receptors on endothelial cells protect the vascular system by release of prostacyclin against platelet aggregation and vasoconstriction. They treat and prevent side effects during administration of prostaglandin antagonists by preference of aspirin. Prostacyclin is triggered here for the first time in response to a pharmaceutical compound.

When [³H]paf was added to endothelial cells prior to unlabelled ligands, such as unlabelled antagonists, unlabelled paf (500 nM) was not inhibitory (4.2 fmol vs. 4.7 fmol, one experiment representative of three). Thus, antagonists are more efficient when they are administered prior or in the absence of paf production during inflammatory reactions, for example. Endothelial cells bound 13.1±2.5 fmol [³H]paf in the presence as compared with 11.3±2.3 fmol in the absence of LA-paf.

An incubation of endothelial cells with lipoproteins, for example, very low density lipoprotein (6%, v/v, final concentration, 3 min at 37° C.) increased the total binding of [³H]paf (0.65 nM) from 11.3±2.3 to 48.5±3 fmol per confluent dish of adherent endothelial cells (n=3). The paf receptor antagonist WEB 2086 was not inhibitory after incubation with lipoproteins as it resulted in 53.2±3.5 fmol bound [³H]paf. Thus, antagonists against very high affinity receptors have to be administered before lipoproteins increase, for example, with or prior to food. The effects of lipoproteins and/or LA-paf are novelties because the known paf binding assays are preformed only in the presence of dilapidated serum albumin.

TABLE I

Specific [³H]paf binding to confluent Huvec determined with specific paf receptor antagonists:

| WEB 2086 | BN 52021 | CV 3988 |
|---|---|---|
| 1 nM 0.7 ± 0.2 | 6 µM 1.6 ± 11.4 | 3 µM 2.2 ± 1.4 |
| 10 nM 1.5 ± 1.1 | 10 µM 4.8 ± 3.5 | 10 µM 2.7 ± 1.9 |
| 1 µM 3.0 ± 0.7 | 60 µM 3.9 ± 3.1 | 30 µM 4.4 ± 1.4 |

Specific [³H]paf binding to endothelial cells was determined as described above using the indicated differences of [³H]paf binding with or without indicated antagonists such as the ginkgolide BN 52021. The antagonists inhibited the [³H]paf binding to endothelial cells. [³H]Paf binding was calculated in fmol [³H]paf bound to $5.2×10^5$ confluent cells. Values are means±1 S.D. of 3 experiments.

EXAMPLE 3

Paf metabolism and cellular LA-paf production 3.1. Endothelial cells

Figure 2A:
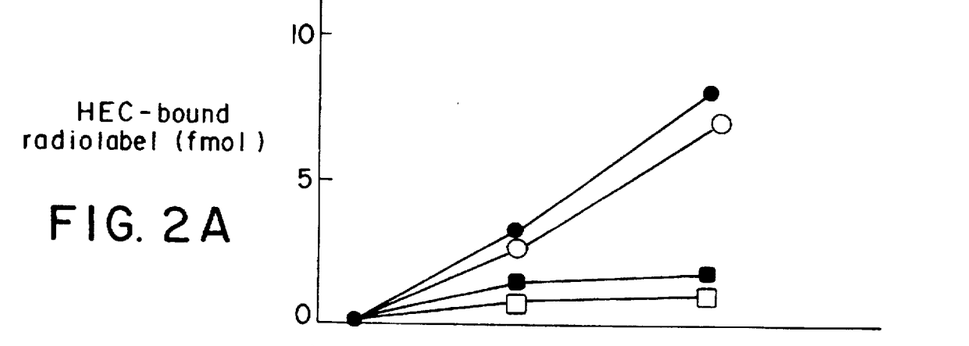
FIG. 2 shows paf metabolism in freshly prepared human umbilical vein endothelial cells.
Figure 2B:
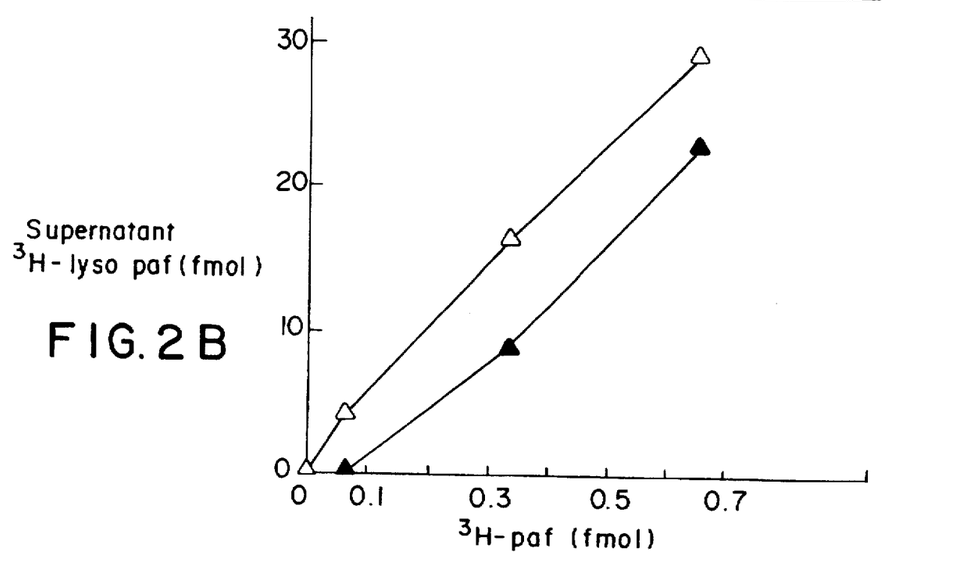

Endothelial cells metabolized exogenously added [³H]paf to compounds comigrating with labelled LA-paf (FIG. 2). According to the invention, endothelial cells metabolized [³H]paf (0.3 or 0.65 nM) because 26 and 17 percent or 16 and 11 percent of added label eluted from standard HPLC together with LA-paf with a retention time of 9–15 min. These long-chain paf metabolites are partially inactive and LA-paf must be further purified. Extraction as well as phospholipid purification with HPLC was performed as described [R. Korth et al. (1989) Brit. J. Pharmacol. 98, 653–661].

The peak comigrating with LA-paf was exclusively found in endothelial cells whereas lyso paf was found in endothelial supernatants. Addition of unlabelled paf decreased the amount of cellular paf metabolites indicating that endothelial paf metabolism and LA-paf production interfere with very high affinity receptors on endothelial cells. According to the invention antagonists are directed against very high affinity paf receptors and LA-paf production. LA-paf and lipoproteins interact also with high affinity paf receptors on blood cells and trigger the production of cellular paf metabolites as shown in the priority document (U.S. patent application Ser. No. 08/104,599).

3.2 Legend for FIG. 2

Concentration-dependent [³H]paf metabolism by endothelial cells and their supernatants. Endothelial cells were incubated with increasing concentrations of [³H]paf as defined in the absence (●■▲) or presence (○□△) of unlabelled paf (500 nM) (30 min, 20° C., 0.25% BSA). Endothelial cells and their supernatants were extracted separately to perform HPLC using standard procedure. Compounds comigrating with Paf (●○) or LA-paf (■□) or lyso paf (▲△) in endothelial cells were calculated in fmol as means of duplicates and are representative of two experiments.

EXAMPLE 4
Use of soluble cells

According to the invention cell lines or soluble cells were used to produce LA-paf. LA-paf was produced in vitro by incubation of soluble cells in the presence of serum. According to the invention soluble cells, for example, cell lines such as cancer cell lines, fungal cells or bacterial cells are suitable whereas the number of freshly prepared endothelial cells is limited. Soluble cells, for example, human histiocyte lymphoma cell lines with monocyte/macrophage like qualities such as U 937 cell line are commercially available.

According to the invention U 937 cells were incubated for example 48 h in 10% foetal calf serum using standard procedure. The biologically active LA-paf was purified with standard phospholipid extraction and HPLC to be quantified using aggregation of rabbit platelets which are washed as described, for example, for human platelets in the priority document [R. Korth, U.S. patent application Ser. No. 08/104,599].

According to the invention soluble cells metabolized exogenously added [³H]paf to compounds comigrating with labelled LA-paf. Resident U 937 cells carried huge amounts of biologically active LA-paf (41 ng LA-PAF per $10^7$ cells). Labelled LA-paf was produced as it eluted together with biologically active LA-paf from standard phase HPLC (Table II). [³H]paf remained intact in the buffer (1 h at 37° C.). [³H]paf degradation in the presence of lipoproteins or in the absence of cells was excluded.

TABLE II

Labelled LA-paf production and cellular [³H]paf metabolism.
The [³H]paf metabolism of U 937 cell lines was investigated.
[³H]paf (2.5 nM) was added for 1 h incubation period at 37°
C to washed cells (2.5 × $10^6$ per ml) before phospholipid analysis.
U 937 cells were cultured, for example, 48 h in the presence of FCS.
Values are percentage of the total labed (166 931 dpm) after subtraction of the background values.

| Percentage (%) | void volume | Retention time: | | |
| --- | --- | --- | --- | --- |
| | | 9–15 min LA-Paf | 18–21 min paf | 28–31 min lyso paf |
| Experiment 1: | 1.8 | 20 | 78 | 0.2 |
| Experiment 2: | 4.5 | 32 | 61 | 2.9 |

Materials

Cells were washed in Tyrode's buffer and materials were used as described [R. Korth et al. (1988) Eur. J. Pharmacol. 152, 101–110; R. Korth et al. (1989) Brit. J. Pharmacol. 98, 653–661]. BSA (fraction V) and PMA were from Sigma (St. Louis, Mo., U.S.A.). Radiolabelled synthetic paf in the position 1 of the molecule ([³H]paf, 80 Ci/mmol) as well as BCS, PCS and OCS scintillation fluid were from Amersham (Amersham, U.K.) and were dissolved in pure ethanol. Unlabelled synthetic paf was from Bachem, (Bubendorf, Switzerland) and solubilized in ethanol. Human Insulin was from Hoechst (Germany). Immortalized human umbilical vein endothelial cells (Im-Huvec) were obtained from Patrick Vicard and Denise Paulin (Institute Pasteur, France) [Llorens Cortes et al. (1992) J. Biol. Chem. 267, 14012–14018]. The human histiocytic lymphoma cell line U 937 was established 1974 by C. Sundstrom and K. Nilsson [Int. J. Cancer 17 (1976), 565–577]. They were obtained from American Type Culture Collection (AtCC 6th Ed. CRL 1593).

Footnotes

Abbreviations used: Lipoprotein-associated platelet activating factor (LA-paf). Low density lipoproteins (LDL), very low density lipoproteins (VLDL) and high density lipoproteins (HDL). Inhibitory fifty percent values ($IC_{50}$). Fatty acid free bovine serum albumin (BSA), acid citrate dextrose (ACD), foetal calf serum (FCS), phorbol-12-myristate-13-acetate (PMA).

Discussion

The invention shows novel methods to test antagonists against LA-paf or very high affinity receptors on endothelial cells. Endothelial cells protect and repair the lining of established blood vessels, create new vessels and prevent thrombosis and/or spastic vasoconstriction [Molecular Biology of the Cell, Eds. Alberts. et al., 2nd ed., 1989, pp 962].

Endothelial cells, for example, immortalized cell lines produce and express very high affinity paf receptors during their differentiation, by preference with insulin. The antagonists are tested with quick and simple methods for their clinical use. Healthy persons with risk factors such as diabetes, obesity, hyperinsulinemia, hyperlipidemia and acid pH values might develop putative disorders some ten years later. These disorders are based on an increased thickness of the basal lamina in the subendothelium, for example, leading to vascular, kidney and heart diseases, neurological disorders such as polyneuropathia and/or blindness. Phospholipids play a role in atherosclerosis [for review D. Steinberg et al. (1989) New Engl. J. Med. 320, 915–924]. Paf-acether (paf, originally platelet activating factor) is a potent inflammatory ether phospholipid, chemically 1-O-alkyl-2-acetyl-sn-glycero-3-phosphocholine with an acetyl group in position 2 and saturated or non-saturated alkyl-groups in position 1 of the molecule [J. Benveniste et al. C.R. Acad. Sci. (Paris) 289, 1037–1040, C. A. Demopoulos et al. (1979) J. Biol. Chem. 254, 9355–9358; R. Korth et al. (1985) Chem. Phys. Lipids 36, 209–214]. Fatty acid free serum albumin is a known paf carrier in the plasma to inhibit platelet activation and paf binding in a non-specific manner [R. Korth and J. Benveniste (1987) Eur. J. Pharmacol. 142, 331–341]. A compound "peak x" has been found in the human plasma using platelet aggregation [J. Benveniste et al. (1988) FEBS Lett. 226, 371–376; J. Benveniste et al. (1987) Fed. Proceedings 46, Abstr. 6719]. However, "peak x" has been identified as being paf in a second high pressure liquid chromatography run (HPLC) leading away from LA-paf. Other oxidized compounds with an ester group in position 1 of the molecule are found in lipoproteins but they are more than 1000 fold less potent as compared with paf [K. E. Stremler et al. (1989) J. Biol. Chem. 264, 5331–5334; C. A. Demopoulos et al. (1979) J. Biol. Chem. 254, 9355–9358].

Specific antagonists against paf receptors on blood cells are known. Triazolothieno-diazepines share similar pharmacological properties with chemically defined extracts of natural Ginkgo biloba, a plant used in the traditional Chinese medicine as treatment against lung and heart diseases. For example, various triazolothieno-diazepines interact with paf receptors on human platelets as the antagonist $IC_{50}$ values correlated closely for platelet paf binding and paf-mediated platelet aggregation (or $Ca^{2+}$ flux) and a parallel rightward shift of the paf dose response curve reaches maximal values with inefficiency of WEB 2086 against platelet aggregation in response to aspirin and ADP [R. Korth et al. (1988) Eur. J. Pharmacol. 152, 101–110; R. Korth et al. (1989) Brit. J. Pharmacol. 98, 653–661].

The "treatment of paf-acether-induced maladies" with ginkgolides has been described before [P. Braquet, U.S. Pat. No. 4,734,280, 1988]. However, the methods therein exclude endothelial cells because "technical details concerning the operative procedure, the induction of focal deendotheliazation" with "a time interval between the beginning of the PAF-Acether superfusion and the first signs of thrombus formation" (page 4). The reference leads clearly away from LA-paf when ginkgolides "exhibit virtually no inhibition against platelet aggregation caused by other factors" (page 1). The severity of the described diseases (posttrauma period on page 2 and shock on page 8) leads away from administration with food or beauty products because these patients do not eat or use beauty products.

Similarly, the application of W. Stransky et al. concerning thieno-1,4-diazepines [U.S. Pat. No. 4,900,729; filing date Feb. 13, 1990] treats disorders caused by chemically defined platelet activating factor to be produced only during inflammation. Other patents refer to chemically defined paf and/or paf antagonists with "excellent platelet activating factor antagonism", for example, of "thiazolidin-4-one derivatives and acid addition salts thereof" [O. Keiichi et al., Eur. Patent Appl. No. 87306508.0].

The above references are silent concerning antagonists against very high affinity receptors on endothelial cells and/or LA-paf binding and production. LA-paf has been shown to be physicochemically and functionally distinct to paf (paf-acether) in the priority document of the present invention [U.S. patent application Ser. No. 08/104,599, FIG. 1]. LA-paf and paf elute with distinct retention times using HPLC and huge amounts of LA-paf in monocyte/macrophage like cells are not recognized by the specific acetylhydrolase. Platelet aggregation cannot distinguish between paf and LA-paf because LA-paf and lipoproteins share a novel receptor not accessible for paf. LA-paf is produced in cells such as platelets and monocytes to be released whereas lipoproteins deacetylate paf to lyso paf but do not produce LA-paf [U.S. patent application Ser. No. 08/104,599, FIGS. 2 to 4, Tables 1 and 2].

Non-differentiated cells express distinct paf, LA-paf and/or lipoprotein receptors during their differentiation as shown here and in the priority document of the present invention [U.S. patent application Ser. No. 08/104,599, FIGS. 4 to 8, Tables 1, 3 to 5]. For example, lipoproteins, cholesterol or LA-paf express high affinity (ha) paf receptors during differentiation of monocyte/macrophage like cells whereas fresh or immortalized endothelial cells after differentiation with insulin express very high affinity (vha) receptors.

The present invention refers to the treatment with antagonists against very high affinity receptors on endothelial cells. Quite surprisingly, antagonists against very high affinity receptors enhance prostacyclin synthesis to further protect the vascular system, for example, of persons during treatment with prostaglandin antagonists, by preference during aspirin treatment.

Finally, in the present invention ginkgolides are administered to healthy persons for the first time with food or beauty products. This is fully supported in the invention because lipoproteins and blood cells as well as freshly prepared endothelial cells of healthy persons carry, bind and produce LA-paf. The invention facilitates to administer natural ginkgolides for example with food and helps to compose "FIDA infants' foods for invalids and seniors" [R. Korth U.S. Trademark Application, Ser. No. 74/416,579, date of filing Jul. 26, 1993]. Then, "FIDA-infants' foods for invalids and seniors" antagonize disorders caused by infection, irritation, differentiation, aging or cell death in vivo. Antagonists can also be administered as beauty products because they trigger creation of new vessels when they prevent irritation, pathological differentiation, aging and death of endothelial cells with degeneration of the perivascular tissue. In the latter case fibroblasts, emigrated blood cells or smooth muscle cells do not increase in the subendothelial to prevent a pathological thickness of the basal lamina. The administration with food or beauty products to healthy persons is supported by the invention because LA-paf is present whereas paf is completely absent. The discoveries are used in the invention to compose and use food or beauty products, for example, with ginkgolides and/or antioxidant compounds such as vitamins to interfere with LA-paf production.

These findings are relevant to conduct quick and simple procedures for the composition of specific antagonists against high and very high affinity receptors for paf and/or LA-paf. The antagonists are administered, by preference with food or beauty products to healthy persons to treat or prevent pathological effects of risk factors.

I claim:

1. A method of treatment or prevention of irritation of endothelial cells, in a subject who is at risk of developing a condition selected from the group consisting of obesity with irritation of the lymphatic system, diabetes, transplantation and polyneuropathy with irritation of the subendothelial tissue, addictive and psychotic diseases with irritation of the endothelial blood brain barrier, skin diseases and fungal phagocytosis, said method comprising administering an effective amount of an antagonist against LA-paf to said subject wherein the antagonist is a composition comprising one or more ginkgolides.

2. The method of claim 1 wherein the antagonists are directed against very high affinity receptors on endothelial cells to prevent and inhibit the binding or production of LA-paf.

3. The method of claim 1 wherein the one or more ginkgolides is a mixture comprising more than one ginkgolides.

4. The method of claim 3 wherein the mixture comprising more than one ginkgolides is BN 52063.

5. The method of claim 1 wherein the composition is administered with food.

6. The method according to claim 5 wherein the ginkgolides are natural ginkgolides and the mixture contains BN 52063.

7. The method of claim 1 wherein the composition is administered with beauty products in a pharmaceutical vehicle of acidic pH value to protect the skin.

8. The method according to claim 7 wherein the ginkgolides are natural ginkgolides and the mixture contains BN 52063.

9. The method of claim 1 wherein the composition protects the vascular system with creation of new vessels of persons with risk factors selected from the group consisting of obesity with irritation of the lymphatic system, diabetes, transplantation and polyneuropathy with irritation of the subendothelial tissue, addictive and psychotic diseases with irritation of the endothelial blood brain barrier, skin diseases and fungal phagocytosis.

10. The method of claim 1 wherein the LA-paf antagonists further comprise an antioxidant.

11. The method of claim 1 wherein the composition comprises a mixture of ginkgolides, antioxidant compounds and vitamins, and is administered to persons with the risk factors selected from the group consisting of obesity with irritation of the lymphatic system, diabetes, transplantation and polyneuropathy with irritation of the subendothelial tissue, addictive and psychotic diseases with irritation of the endothelial blood brain barrier skin diseases, and fungal phagocytosis, to protect the vascular system, the endothelial blood brain barrier, against an irritation of the subendothelial tissue, and against an increased thickness of the basal lamina.

* * * * *